(12) United States Patent
Zhang et al.

(10) Patent No.: US 9,647,550 B2
(45) Date of Patent: May 9, 2017

(54) NEGATIVE VOLTAGE SIGNAL GENERATION CIRCUIT

(71) Applicant: SHENZHEN CHINA STAR OPTOELECTRONICS TECHNOLOGY CO., LTD., Shenzhen (CN)

(72) Inventors: Hua Zhang, Guangdong (CN); Dan Cao, Guangdong (CN)

(73) Assignee: SHENZHEN CHINA STAR OPTOELECTRONICS TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 14/769,176

(22) PCT Filed: May 25, 2015

(86) PCT No.: PCT/CN2015/079727
§ 371 (c)(1),
(2) Date: Aug. 20, 2015

(87) PCT Pub. No.: WO2016/179855
PCT Pub. Date: Nov. 17, 2016

(65) Prior Publication Data
US 2015/0381050 A1    Dec. 31, 2015

(30) Foreign Application Priority Data

May 11, 2015  (CN) .......................... 2015 1 0236631

(51) Int. Cl.
*H02M 3/158* (2006.01)
*A61B 5/00* (2006.01)

(52) U.S. Cl.
CPC .......... *H02M 3/158* (2013.01); *A61B 5/4538* (2013.01)

(58) Field of Classification Search
CPC .. H02M 2001/009; H02M 3/07; H02M 3/158; H02M 3/073; H02M 3/155; Y10T 307/839; Y10T 307/931; G05F 1/56; G11C 16/30; G11C 5/145
See application file for complete search history.

(56) References Cited

U.S. PATENT DOCUMENTS

| | | | | |
|---|---|---|---|---|
| 4,338,656 A * | 7/1982 | Yamakido | ................. | G05F 1/56 307/127 |
| 5,999,426 A * | 12/1999 | Meier | ................... | H04M 19/08 323/222 |
| 6,184,741 B1 * | 2/2001 | Ghilardelli | ............. | G11C 5/145 327/536 |
| 2002/0089369 A1 * | 7/2002 | Ikeda | ...................... | H02M 3/07 327/536 |

(Continued)

*Primary Examiner* — Adolf Berhane
*Assistant Examiner* — Henry Lee, III
(74) *Attorney, Agent, or Firm* — Osha Liang LLP

(57) ABSTRACT

A negative voltage signal generation circuit is described. The first thin film transistor (TFT) connects the first ground terminal to the control signal generation unit. The second TFT switch connects to the first TFT switch, the control signal generation unit and the negative voltage signal output terminal. The first capacitor connects to the first TFT switch, the second TFT switch and the control signal generation unit. The present invention is capable of improving the stability of the negative voltage signal generation circuit.

20 Claims, 3 Drawing Sheets

(56) References Cited

U.S. PATENT DOCUMENTS

| | | | | |
|---|---|---|---|---|
| 2008/0303586 A1* | 12/2008 | Li | ............................ | H02M 3/07 327/536 |
| 2010/0013445 A1* | 1/2010 | Martinussen | ............ | H02M 3/07 323/234 |
| 2010/0039170 A1* | 2/2010 | Ryoo | ....................... | H02M 3/07 327/538 |
| 2013/0328597 A1* | 12/2013 | Cassia | ..................... | G11C 5/145 327/109 |

* cited by examiner

NEGATIVE VOLTAGE SIGNAL GENERATION CIRCUIT

BACKGROUND OF THE INVENTION

Field of Invention

The present invention relates to a technical field of a driving circuit, and more particularly to a negative voltage signal generation circuit.

Description of Prior Art

Conventionally, a driving circuit of a display panel includes a negative voltage signal generation circuit for generating a negative voltage signal.

In the prior art of generation circuit, the response speed of negative voltage signal generation circuit is lower, which downgrades the accuracy of voltage values corresponding to the generated negative voltage signal.

Furthermore, the endurance power value of the conventional negative voltage signal generation circuit is lower, which affects the stability of the whole negative voltage signal generation circuit disadvantageously.

Consequently, there is a need to develop a novel technical scheme to solve the afore-mentioned problems.

SUMMARY OF THE INVENTION

One objective of the present invention is to provide a negative voltage signal generation circuit to improve the stability of negative voltage signal generation circuit.

According to the above objective, the present invention sets forth a negative voltage signal generation circuit a negative voltage signal generation circuit, comprising: a negative voltage signal output terminal; a first ground terminal; a control signal generation unit, for generating a first control signal and a second control signal; a first thin film transistor (TFT) switch comprising a first gate electrode, a first source electrode and a first drain electrode, wherein the first TFT switch connects to the first ground terminal and the control signal generation unit, and the first TFT switch turns on/off a first current channel between the first source electrode and the first drain electrode according to on/off statuses of the first control signal; a second TFT switch comprising a second gate electrode, a second source electrode and a second drain electrode, wherein the second TFT switch connects to the first TFT switch, the control signal generation unit and the negative voltage signal output terminal, and the second TFT switch turns on/off a second current channel between the second source electrode and the second drain electrode according to on/off statuses of the second control signal; and a first capacitor comprising a first pole plate and a second pole plate, wherein the first pole plate connects to a first connection wire between the first TFT switch and the second TFT switch, and the second pole plate is connected to the control signal generation unit; wherein the second current channel is turned off when the first current channel is turned on, and the second current channel is turned on when the first current channel is turned off; wherein the first gate electrode is connected to the control signal generation unit for receiving the first control signal, either the first source electrode or the first drain electrode is connected to the first ground terminal, and either the first source electrode or the first drain electrode is connected to the second TFT switch; wherein the second gate electrode is connected to the control signal generation unit for receiving the second control signal, either the second source electrode or the second drain electrode is connected to the first TFT switch, and either the second source electrode or the second drain electrode is connected to the negative voltage signal output terminal; wherein the first pole plate electrically connects to the first ground terminal when the first current channel is turned on; wherein the second pole plate is charged by electrical charges which correspond to the first control signal issued from the control signal generation unit when the first current channel is turned on; wherein a voltage level corresponding to the second pole plate is changed to zero when the first current channel is turned off; wherein a voltage level corresponding to the first pole plate is changed to a negative voltage level for generating a negative voltage signal when the first current channel is turned off; wherein the second TFT switch outputs the negative voltage signal when the first current channel is turned off; the negative voltage signal generation circuit further comprising: a regulation resistor comprising a first terminal and a second terminal wherein the first terminal connects to the second TFT switch, the second terminal connects to the negative voltage signal output terminal, and the regulation resistor regulates a current magnitude of the negative voltage signal; the control signal generation unit comprising a control signal generator and a phase inverter; wherein the control signal generator connects to the first gate electrode, the second pole plate and an inversion input terminal of the phase inverter respectively, and an inversion output terminal of the phase inverter connects to the second gate electrode; either wherein the second control signal is formed by inverting the first control signal so that the control signal generator forms the first control signal for outputting the first control signal to allow the phase inverter to invert the first control signal for forming the second control signal or wherein the first control signal is formed by inverting the second control signal so that the control signal generator forms the second control signal for outputting the second control signal to allow the phase inverter to invert the second control signal for forming the first control signal; and the control signal generation unit further comprising a duty ration controller for controlling a duty ratio of the first control signal and/or the second control signal in order to control a turn-on duration time of the second current channel.

In the negative voltage signal generation circuit, the second control signal is in a low level when the first control signal is in a high level, the second control signal is in the high level when the first control signal is in the low level, and the first TFT switch and the second TFT switch are selected from one group consisting of a positive channel metal-oxide-semiconductor (PMOS) and a negative channel metal-oxide-semiconductor (NMOS).

In the negative voltage signal generation circuit, the first control signal and the second control signal are the same signal, the first TFT switch is one of PMOS and NMOS, and the second TFT switch is the other of the PMOS and the NMOS.

In the negative voltage signal generation circuit of claim 1, further comprising: a second ground terminal; and a second capacitor comprising a third pole plate and a fourth pole plate, wherein the third pole plate connects to a second connection wire between the regulation resistor and the negative voltage signal output terminal, and the fourth pole plate connects to the second ground terminal.

A negative voltage signal generation circuit comprises: a negative voltage signal output terminal; a first ground terminal; a control signal generation unit, for generating a first control signal and a second control signal; a first TFT switch comprising a first gate electrode, a first source electrode and a first drain electrode, wherein the first TFT switch connects to the first ground terminal and the control signal generation unit, and the first TFT switch turns on/off a first current channel between the first source electrode and the first drain electrode according to on/off statuses of the first control signal; a second TFT switch comprising a second gate electrode, a second source electrode and a second drain electrode, wherein the second TFT switch connects to the first TFT switch, the control signal generation unit and the negative voltage signal output terminal, and the second TFT switch turns on/off a second current channel between the second source electrode and the second drain electrode according to on/off statuses of the second control signal; and a first capacitor comprising a first pole plate and a second pole plate, wherein the first pole plate connects to a first connection wire between the first TFT switch and the second TFT switch, and the second pole plate is connected to the control signal generation unit; wherein the second current channel is turned off when the first current channel is turned on, and the second current channel is turned on when the first current channel is turned off.

In the negative voltage signal generation circuit, the first gate electrode connected to the control signal generation unit receives the first control signal, one of the first source electrode and the first drain electrode is connected to the first ground terminal, and one of the first source electrode and the first drain electrode is connected to the second TFT switch; and wherein the second gate electrode connected to the control signal generation unit receives the second control signal, one of the second source electrode and the second drain electrode is connected to the first TFT switch, and one of the second source electrode and the second drain electrode is connected to the negative voltage signal output terminal.

In the negative voltage signal generation circuit, the first pole plate electrically connects to the first ground terminal when the first current channel is turned on; and wherein the second pole plate is charged by electrical charges which correspond to the first control signal issued from the control signal generation unit when the first current channel is turned on.

In the negative voltage signal generation circuit, a voltage level corresponding to the second pole plate is changed to zero when the first current channel is turned off; wherein a voltage level corresponding to the first pole plate is changed to a negative voltage level for generating a negative voltage signal when the first current channel is turned off; and wherein the second TFT switch outputs the negative voltage signal when the first current channel is turned off.

In the negative voltage signal generation circuit, the second control signal is in a low level when the first control signal is in a high level, and the second control signal is in the high level when the first control signal is in the low level.

In the negative voltage signal generation circuit, the first TFT switch and the second TFT switch are a PMOS.

In the negative voltage signal generation circuit, the first TFT switch and the second TFT switch are a NMOS.

In the negative voltage signal generation circuit, the first control signal and the second control signal are the same signal.

In the negative voltage signal generation circuit, the first TFT switch is a PMOS and the second TFT switch is a NMOS.

In the negative voltage signal generation circuit, the first TFT switch is a NMOS and the second TFT switch is a PMOS.

The negative voltage signal generation circuit further comprises a regulation resistor having a first terminal and a second terminal wherein the first terminal connects to the second TFT switch, the second terminal connects to the negative voltage signal output terminal, and the regulation resistor regulates a current magnitude of the negative voltage signal.

The negative voltage signal generation circuit further comprises a second ground terminal; and a second capacitor comprising a third pole plate and a fourth pole plate, wherein the third pole plate connects to a second connection wire between the regulation resistor and the negative voltage signal output terminal, and the fourth pole plate connects to the second ground terminal.

In the negative voltage signal generation circuit, the control signal generation unit comprises a control signal generator and a phase inverter; and wherein the control signal generator connects to the first gate electrode, the second pole plate and an inversion input terminal of the phase inverter respectively, and an inversion output terminal of the phase inverter connects to the second gate electrode.

In the negative voltage signal generation circuit, the second control signal is formed by inverting the first control signal so that the control signal generator forms the first control signal for outputting the first control signal to allow the phase inverter to invert the first control signal for forming the second control signal.

In the negative voltage signal generation circuit, the first control signal is formed by inverting the second control signal so that the control signal generator forms the second control signal for outputting the second control signal to allow the phase inverter to invert the second control signal for forming the first control signal.

In the negative voltage signal generation circuit, the control signal generation unit further comprises a duty ration controller for controlling a duty ratio of the first control signal and/or the second control signal in order to control a turn-on duration time of the second current channel.

In comparison with conventional technical art, the present invention is capable of improving the stability of the negative voltage signal generation circuit.

The foregoing aspects and many of the attendant advantages of this invention will become more readily appreciated as the same becomes better understood by reference to the following detailed description, when taken in conjunction with the accompanying drawings.

DETAILED DESCRIPTION OF THE PREFERRED EMBODIMENTS

The negative voltage signal generation circuit of the present invention is applicable to a driving circuit in the display panel wherein the display panel may be a thin film transistor liquid crystal display (TFT-LCD) and an organic light emitting diode (OLED).

Figure 1:
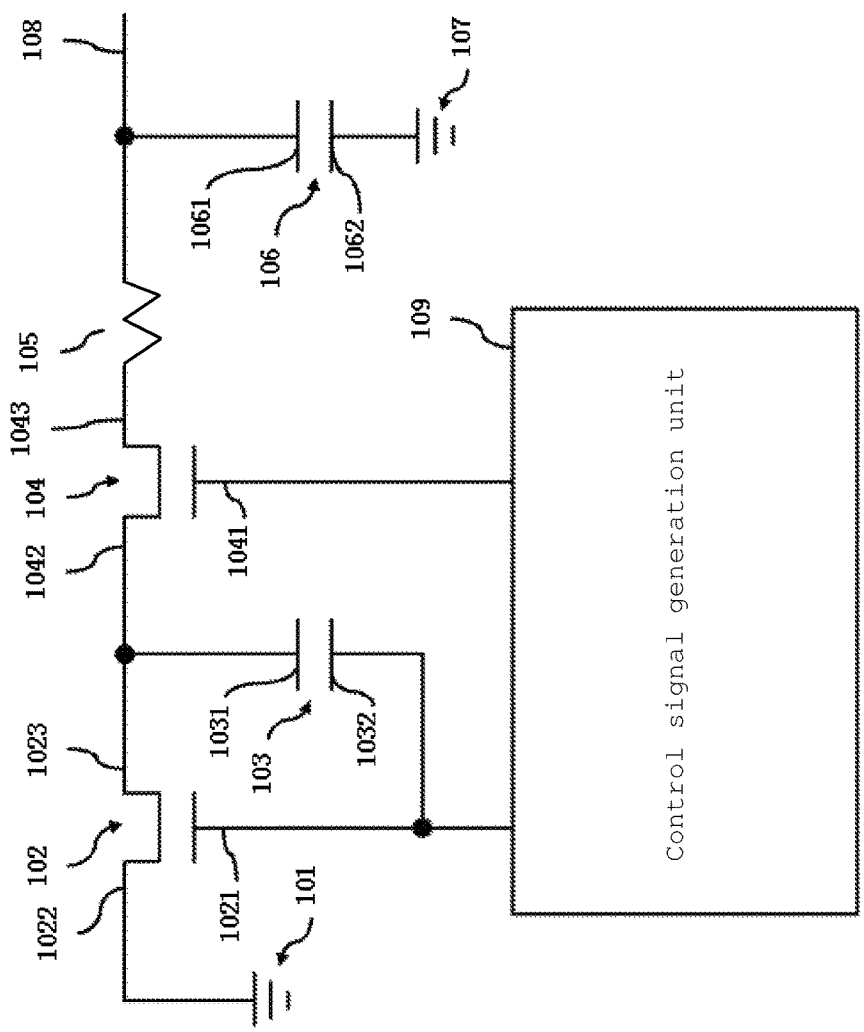
FIG. 1 is a schematic circuit view of a negative voltage signal generation circuit according to a first embodiment of the present invention.

Refer to FIG. 1, which is a schematic circuit view of a negative voltage signal generation circuit according to a first embodiment of the present invention. In this embodiment, the negative voltage signal generation circuit comprises a negative voltage signal output terminal 108, a first ground terminal 101, a control signal generation unit 109, a first thin film transistor (TFT) switch 102, a second TFT switch 104 and a first capacitor 103.

The control signal generation unit 109 is used to generate a first control signal and a second control signal.

The first TFT switch 102 comprises a first gate electrode 1021, a first source electrode 1022 and a first drain electrode 1023. The first TFT switch 102 connects to the first ground terminal 101 and the control signal generation unit 109. The first TFT switch 102 turns on/off a first current channel between the first source electrode 1022 and the first drain electrode 1023 according to on/off statuses of the first control signal.

The second TFT switch 104 comprises a second gate electrode 1041, a second source electrode 1042 and a second drain electrode 1043. The second TFT switch 104 connects to the first TFT switch 102, the control signal generation unit 109 and the negative voltage signal output terminal 108. The second TFT switch 104 turns on/off a second current channel between the second source electrode 1042 and the second drain electrode 1043 according to on/off statuses of the second control signal.

The first capacitor 103 comprises a first pole plate 1031 and a second pole 1032 plate wherein the first pole plate 1031 connects to a first connection wire between the first TFT switch 102 and the second TFT switch 104, and the second pole plate 1032 is connected to the control signal generation unit 109.

The second current channel is turned off when the first current channel is turned on, and the second current channel is turned on when the first current channel is turned off.

In this embodiment, the first gate electrode 1021 is connected to the control signal generation unit 109 for receiving the first control signal. Either the first source electrode 1022 or the first drain electrode 1023 is connected to the first ground terminal 101, and either the first source electrode 1022 or the first drain electrode is connected to the second TFT switch 102.

The second gate electrode 1041 is connected to the control signal generation unit 109 for receiving the second control signal. Either the second source electrode 1042 or the second drain electrode 1043 is connected to the first TFT switch 102, and either the second source electrode 1042 or the second drain electrode 1043 is connected to the negative voltage signal output terminal 108.

In this embodiment, the first pole plate 1031 electrically connects to the first ground terminal 101 when the first current channel is turned on. The second pole plate 1032 is charged by electrical charges which correspond to the first control signal issued from the control signal generation unit 109 when the first current channel is turned on.

In this embodiment, a voltage level corresponding to the second pole plate 1032 is changed to zero when the first current channel is turned off. A voltage level corresponding to the first pole plate 1031 is changed to a negative voltage level for generating a negative voltage signal when the first current channel is turned off. The second TFT switch 104 outputs the negative voltage signal when the first current channel is turned off.

In this embodiment, the negative voltage signal generation circuit 105 further comprises a regulation resistor 105 having a first terminal and a second terminal wherein the first terminal connects to the second TFT switch 104, the second terminal connects to the negative voltage signal output terminal 108, and the regulation resistor 105 regulates a current magnitude of the negative voltage signal.

In this embodiment, the negative voltage signal generation circuit further comprises a second ground terminal 107 and a second capacitor 106 having a third pole plate 1061 and a fourth pole plate 1062. The third pole plate 1061 connects to a second connection wire between the regulation resistor 105 and the negative voltage signal output terminal 108, and the fourth pole plate 1062 connects to the second ground terminal 107.

In this embodiment, the first control signal and the second control signal are the same signal.

The first TFT switch 102 is either a positive channel metal oxide semiconductor (PMOS) or a negative channel metal oxide semiconductor (NMOS) NMOS, and the second TFT switch 104 is the other of the PMOS and the NMOS.

According to the afore-mentioned descriptions, the present invention is capable of reducing power loss of the negative voltage signal generation circuit and improving stability of the negative voltage signal generation circuit.

The negative voltage signal generation circuit in the second embodiment is similar to that in the first embodiment. The difference between the second embodiment and the first embodiment is that the second control signal is in a low level when the first control signal is in a high level, and the second control signal is in the high level when the first control signal is in the low level.

The first TFT switch 102 and the second TFT switch 104 are selected from one group consisting of a PMOS and a NMOS. In one case, the first TFT switch 102 and the second TFT switch 104 are a PMOS. In another case, the first TFT switch 102 and the second TFT switch 104 are a NMOS.

Figure 2:
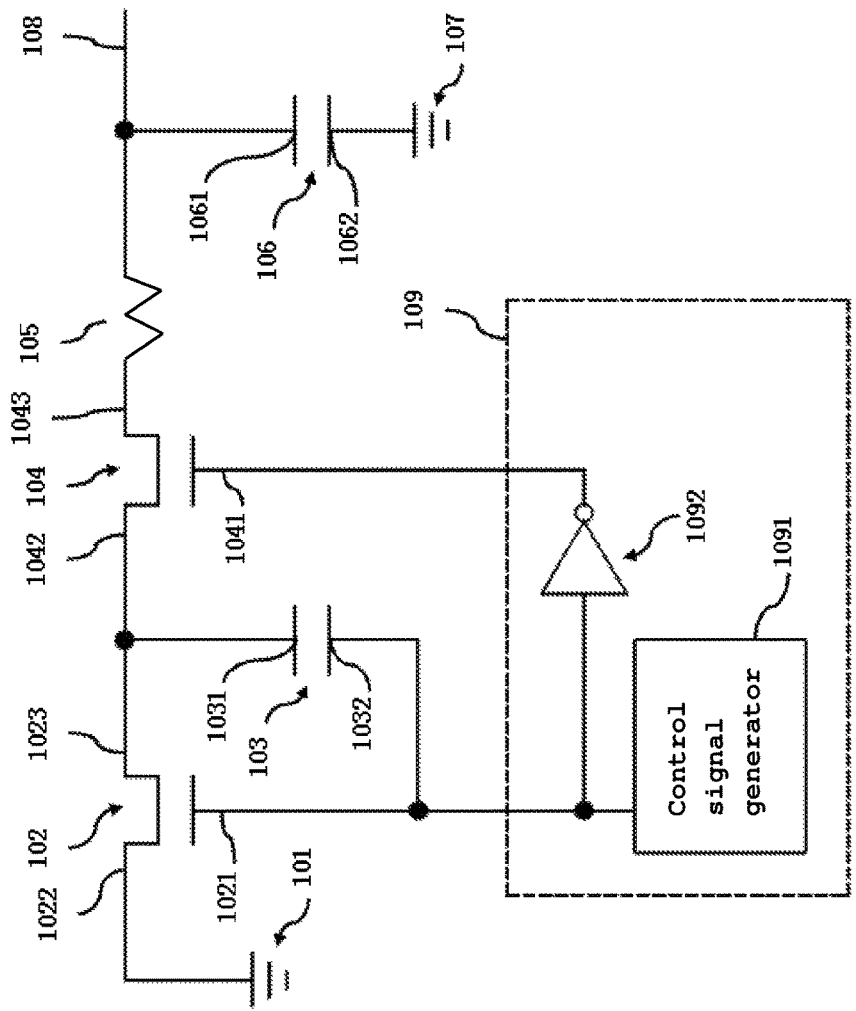
FIG. 2 is a schematic circuit view of a negative voltage signal generation circuit according to a third embodiment of the present invention.

Refer to FIG. 2, which is a schematic circuit view of a negative voltage signal generation circuit according to a third embodiment of the present invention. The negative voltage signal generation circuit in the third embodiment is similar to that in the second embodiment. The difference between the third embodiment and the second embodiment is that the control signal generation unit 109 comprises a control signal generator 1091 and a phase inverter 1092.

The control signal generator 1091 connects to the first gate electrode 1021, the second pole plate 1032 and an inversion input terminal of the phase inverter 1092 respectively, and an inversion output terminal of the phase inverter 1092 connects to the second gate electrode 1041.

The second control signal is formed by inverting the first control signal so that the control signal generator 1091 forms the first control signal for outputting the first control signal to allow the phase inverter 1092 to invert the first control signal for forming the second control signal. The first control signal is formed by inverting the second control signal so that the control signal generator 1091 forms the second control signal for outputting the second control signal to allow the phase inverter 1092 to invert the second control signal for forming the first control signal.

Figure 3:
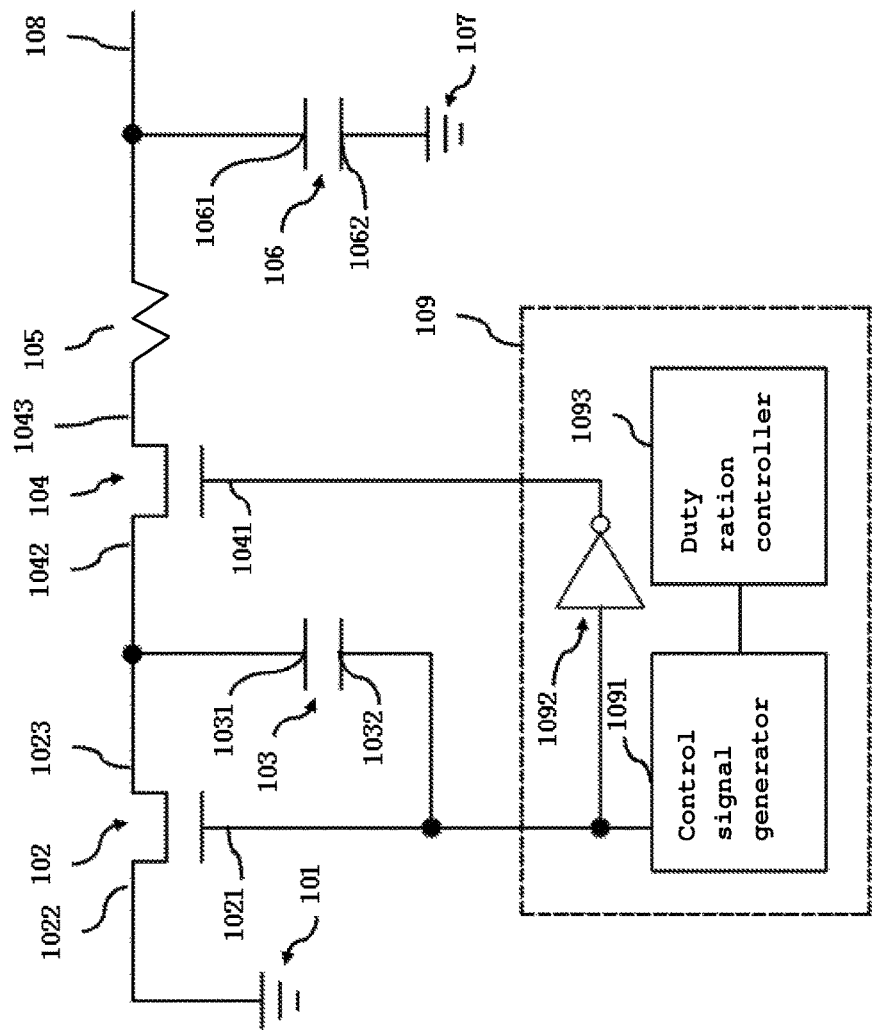
FIG. 3 is a schematic circuit view of a negative voltage signal generation circuit according to a fourth embodiment of the present invention.

Refer to FIG. 3, which is a schematic circuit view of a negative voltage signal generation circuit according to a fourth embodiment of the present invention. The negative voltage signal generation circuit in the fourth embodiment is similar to any one of the first through third embodiments. The difference between the third embodiment and the second embodiment is that the control signal generation unit 109 further comprises a duty ration controller 1093 for controlling a duty ratio of the first control signal and/or the second control signal in order to control a turn-on duration time of the second current channel.

Based on the above descriptions in the fourth embodiment, the current magnitude passing through the first TFT switch and the second TFT switch is regulated by adjusting the duty ratio of the first control signal and/or the second control signal (i.e. the MOS driving signal) to reduce the power loss of the negative voltage signal generation circuit advantageously.

As is understood by a person skilled in the art, the foregoing preferred embodiments of the present invention are illustrative rather than limiting of the present invention. It is intended that they cover various modifications and similar arrangements be included within the spirit and scope of the present invention, the scope of which should be accorded the broadest interpretation so as to encompass all such modifications and similar structures.

What is claimed is:

1. A negative voltage signal generation circuit, comprising:
   a negative voltage signal output terminal;
   a first ground terminal;
   a control signal generation unit, for generating a first control signal and a second control signal;
   a first thin film transistor (TFT) switch comprising a first gate electrode, a first source electrode and a first drain electrode, wherein the first TFT switch connects to the first ground terminal and the control signal generation unit, and the first TFT switch turns on/off a first current channel between the first source electrode and the first drain electrode according to on/off statuses of the first control signal;
   a second TFT switch comprising a second gate electrode, a second source electrode and a second drain electrode, wherein the second TFT switch connects to the first TFT switch, the control signal generation unit and the negative voltage signal output terminal, and the second TFT switch turns on/off a second current channel between the second source electrode and the second drain electrode according to on/off statuses of the second control signal; and
   a first capacitor comprising a first pole plate and a second pole plate, wherein the first pole plate connects to a first connection wire between the first TFT switch and the second TFT switch, and the second pole plate is connected to the control signal generation unit;
   wherein the second current channel is turned off when the first current channel is turned on, and the second current channel is turned on when the first current channel is turned off;
   wherein the first gate electrode is connected to the control signal generation unit for receiving the first control signal, either the first source electrode or the first drain electrode is connected to the first ground terminal, and either the first source electrode or the first drain electrode is connected to the second TFT switch;
   wherein the second gate electrode is connected to the control signal generation unit for receiving the second control signal, either the second source electrode or the second drain electrode is connected to the first TFT switch, and either the second source electrode or the second drain electrode is connected to the negative voltage signal output terminal;
   wherein the first pole plate electrically connects to the first ground terminal when the first current channel is turned on;
   wherein the second pole plate is charged by electrical charges which correspond to the first control signal issued from the control signal generation unit when the first current channel is turned on;
   wherein a voltage level corresponding to the second pole plate is changed to zero when the first current channel is turned off;
   wherein a voltage level corresponding to the first pole plate is changed to a negative voltage level for generating a negative voltage signal when the first current channel is turned off;
   wherein the second TFT switch outputs the negative voltage signal when the first current channel is turned off;
   the negative voltage signal generation circuit further comprising:
   a regulation resistor comprising a first terminal and a second terminal wherein the first terminal connects to the second TFT switch, the second terminal connects to the negative voltage signal output terminal, and the regulation resistor regulates a current magnitude of the negative voltage signal;
   the control signal generation unit comprising a control signal generator and a phase inverter;
   wherein the control signal generator connects to the first gate electrode, the second pole plate and an inversion input terminal of the phase inverter respectively, and an inversion output terminal of the phase inverter connects to the second gate electrode;
   either wherein the second control signal is formed by inverting the first control signal so that the control signal generator forms the first control signal for outputting the first control signal to allow the phase inverter to invert the first control signal for forming the second control signal or wherein the first control signal is formed by inverting the second control signal so that the control signal generator forms the second control signal for outputting the second control signal to allow the phase inverter to invert the second control signal for forming the first control signal; and
   the control signal generation unit further comprising a duty ration controller for controlling a duty ratio of the first control signal and/or the second control signal in order to control a turn-on duration time of the second current channel.

2. The negative voltage signal generation circuit of claim 1, wherein the second control signal is in a low level when the first control signal is in a high level, the second control signal is in the high level when the first control signal is in the low level, and the first TFT switch and the second TFT switch are selected from one group consisting of a positive channel metal-oxide-semiconductor (PMOS) and a negative channel metal-oxide-semiconductor (NMOS).

3. The negative voltage signal generation circuit of claim 1, wherein the first control signal and the second control signal are the same signal, the first TFT switch is one of PMOS and NMOS, and the second TFT switch is the other of the PMOS and the NMOS.

4. The negative voltage signal generation circuit of claim 1, further comprising:
   a second ground terminal; and
   a second capacitor comprising a third pole plate and a fourth pole plate, wherein the third pole plate connects to a second connection wire between the regulation resistor and the negative voltage signal output terminal, and the fourth pole plate connects to the second ground terminal.

5. A negative voltage signal generation circuit, comprising:

a negative voltage signal output terminal;
a first ground terminal;
a control signal generation unit, for generating a first control signal and a second control signal;
a first TFT switch comprising a first gate electrode, a first source electrode and a first drain electrode, wherein the first TFT switch connects to the first ground terminal and the control signal generation unit, and the first TFT switch turns on/off a first current channel between the first source electrode and the first drain electrode according to on/off statuses of the first control signal;
a second TFT switch comprising a second gate electrode, a second source electrode and a second drain electrode, wherein the second TFT switch connects to the first TFT switch, the control signal generation unit and the negative voltage signal output terminal, and the second TFT switch turns on/off a second current channel between the second source electrode and the second drain electrode according to on/off statuses of the second control signal; and
a first capacitor comprising a first pole plate and a second pole plate, wherein the first pole plate connects to a first connection wire between the first TFT switch and the second TFT switch, and the second pole plate is connected to the control signal generation unit;
wherein the second current channel is turned off when the first current channel is turned on, and the second current channel is turned on when the first current channel is turned off.

6. The negative voltage signal generation circuit of claim 5, wherein the first gate electrode connected to the control signal generation unit receives the first control signal, one of the first source electrode and the first drain electrode is connected to the first ground terminal, and one of the first source electrode and the first drain electrode is connected to the second TFT switch; and
wherein the second gate electrode connected to the control signal generation unit receives the second control signal, one of the second source electrode and the second drain electrode is connected to the first TFT switch, and one of the second source electrode and the second drain electrode is connected to the negative voltage signal output terminal.

7. The negative voltage signal generation circuit of claim 6, wherein the first pole plate electrically connects to the first ground terminal when the first current channel is turned on; and
wherein the second pole plate is charged by electrical charges which correspond to the first control signal issued from the control signal generation unit when the first current channel is turned on.

8. The negative voltage signal generation circuit of claim 6, wherein a voltage level corresponding to the second pole plate is changed to zero when the first current channel is turned off;
wherein a voltage level corresponding to the first pole plate is changed to a negative voltage level for generating a negative voltage signal when the first current channel is turned off; and
wherein the second TFT switch outputs the negative voltage signal when the first current channel is turned off.

9. The negative voltage signal generation circuit of claim 5, wherein the second control signal is in a low level when the first control signal is in a high level, and the second control signal is in the high level when the first control signal is in the low level.

10. The negative voltage signal generation circuit of claim 9, wherein the first TFT switch and the second TFT switch are a PMOS.

11. The negative voltage signal generation circuit of claim 9, wherein the first TFT switch and the second TFT switch are a NMOS.

12. The negative voltage signal generation circuit of claim 5, wherein the first control signal and the second control signal are the same signal.

13. The negative voltage signal generation circuit of claim 12, wherein the first TFT switch is a PMOS and the second TFT switch is a NMOS.

14. The negative voltage signal generation circuit of claim 12, wherein the first TFT switch is a NMOS and the second TFT switch is a PMOS.

15. The negative voltage signal generation circuit of claim 5, further comprising a regulation resistor having a first terminal and a second terminal wherein the first terminal connects to the second TFT switch, the second terminal connects to the negative voltage signal output terminal, and the regulation resistor regulates a current magnitude of the negative voltage signal.

16. The negative voltage signal generation circuit of claim 15, further comprising:
a second ground terminal; and
a second capacitor comprising a third pole plate and a fourth pole plate, wherein the third pole plate connects to a second connection wire between the regulation resistor and the negative voltage signal output terminal, and the fourth pole plate connects to the second ground terminal.

17. The negative voltage signal generation circuit of claim 5, wherein the control signal generation unit comprising a control signal generator and a phase inverter; and
wherein the control signal generator connects to the first gate electrode, the second pole plate and an inversion input terminal of the phase inverter respectively, and an inversion output terminal of the phase inverter connects to the second gate electrode.

18. The negative voltage signal generation circuit of claim 17, wherein the second control signal is formed by inverting the first control signal so that the control signal generator forms the first control signal for outputting the first control signal to allow the phase inverter to invert the first control signal for forming the second control signal.

19. The negative voltage signal generation circuit of claim 17, wherein the first control signal is formed by inverting the second control signal so that the control signal generator forms the second control signal for outputting the second control signal to allow the phase inverter to invert the second control signal for forming the first control signal.

20. The negative voltage signal generation circuit of claim 17, wherein the control signal generation unit further comprises a duty ration controller for controlling a duty ratio of the first control signal and/or the second control signal in order to control a turn-on duration time of the second current channel.

* * * * *